United States Patent
Khan

(10) Patent No.: US 12,121,561 B1
(45) Date of Patent: Oct. 22, 2024

(54) COMPOSITION FOR TREATING OR PREVENTING INSULIN RESISTANCE

(71) Applicant: KING FAISAL UNIVERSITY, Al-Ahsa (SA)

(72) Inventor: Gausal Azam Khan, Al Hofof (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/444,663

(22) Filed: Feb. 17, 2024

(51) Int. Cl.
*A61K 39/00* (2006.01)
*A61K 38/02* (2006.01)

(52) U.S. Cl.
CPC .......... *A61K 38/02* (2013.01); *A61K 39/0005* (2013.01)

(58) Field of Classification Search
None
See application file for complete search history.

(56) References Cited

U.S. PATENT DOCUMENTS

| | | |
|---|---|---|
| 7,871,617 B2 | 1/2011 | Lin et al. |
| 8,236,315 B2 | 8/2012 | Lazarides et al. |
| 10,663,462 B2 | 5/2020 | Pfuetzner et al. |

FOREIGN PATENT DOCUMENTS

| | | | |
|---|---|---|---|
| WO | WO8606096 | * | 10/1986 |

OTHER PUBLICATIONS

Riba et al., "von Willebrand factor activates endothelial nitric oxide synthase in blood platelets by a glycoprotein Ib-dependent mechanism," Journal of Thrombosis and Haemostasis, 4: 2636-2644 (Year: 2006).*

Bandana Singh, Indranil Biswas, Iti Garg, Ragumani Sugadev, Abhay K. Singh, Sharmistha Dey, and Gausal A. Khan, "von Willebrand Factor Antagonizes Nitric Oxide Synthase to Promote Insulin Resistance during Hypoxia", https://doi.org/10.1021/bi401061e; 2014.

Lulu Zhang, Jian Su, Fei Shen, Zhenni Ma, Yiming Zhao, Lijun Xia, and Changgeng Ruan, "A novel monoclonal antibody against the von Willebrand Factor A2 domain reduces its cleavage by ADAMTS13", DOI: 10.1186/s13045-017-0407-1; 2017.

Lan Wei, Frank Mckeon, Joshua W. Russo, Joan Lemire, and John Castellot, "Domain- and species-specific monoclonal antibodies recognize the Von Willebrand Factor-C domain of CCN5", DOI: 10.1007/s12079-009-0054-6; 2009.

David S Frankel, James B. Meigs, Joseph M. Massaro, Peter W. F. Wilson, Christopher J. O'Donnell, Ralph B. D'Agostino, and Geoffrey H. Tofler, "Von Willebrand factor, type 2 diabetes mellitus, and risk of cardiovascular disease: the framingham offspring study.", DOI: 10.1161/CIRCULATIONAHA.108.792986; 2008.

* cited by examiner

*Primary Examiner* — M Franco G Salvoza
(74) *Attorney, Agent, or Firm* — Nath, Goldberg & Meyer; Joshua B. Goldberg

(57) ABSTRACT

A composition for treating or preventing insulin resistance in a subject, the composition comprising a peptide of SEQ ID NO: 1 and a pharmaceutically acceptable carrier or adjuvant.

6 Claims, No Drawings

Specification includes a Sequence Listing.

COMPOSITION FOR TREATING OR PREVENTING INSULIN RESISTANCE

INCORPORATION BY REFERENCE OF MATERIAL SUBMITTED IN COMPUTER READABLE FORM

The Applicants hereby incorporate by reference the sequence listing contained in the XML file titled 33155_64u_sequence.xml, created Feb. 11, 2024 and having 2000 bytes of data.

BACKGROUND

1. Field

The present disclosure relates to a method of treating or preventing insulin resistance and, particularly, to a method of treating insulin resistance using a peptide.

2. Description of the Related Art

Von Willebrand Factor (vWF) is a multimeric adhesive glycoprotein present in the plasma of mammals, which has multiple physiological functions. During primary hemostasis, Von Willebrand Factor (vWF) acts as a mediator between specific receptors on the platelet surface and components of the extracellular matrix such as collagen. Moreover, Von Willebrand Factor (vWF) serves as a carrier and stabilizing protein for procoagulant Factor VIII. Von Willebrand Factor (vWF) is synthesized in endothelial cells and megakaryocytes as a 2813 amino acid precursor molecule. The precursor polypeptide, pre-pro-Von Willebrand Factor, consists of a 22-residue signal peptide, a 741-residue propeptide and the 2050-residue polypeptide found in mature plasma Von Willebrand Factor (Fischer et al., FEBS Lett. 351:345-348, 1994).

Upon secretion into plasma, Von Willebrand Factor (vWF) circulates in the form of various species with different molecular sizes. These Von Willebrand Factor (vWF) molecules consist of oligo- and multimers of the mature subunit of 2050 amino acid residues. Von Willebrand Factor (vWF) can be usually found in plasma as multimers ranging in size approximately from 500 to 20,000 kDa (Furlan, Ann Hematol. 1996 June; 72 (6): 341-8).

Vaccines are common therapies for preventing infectious diseases. For example, vaccines have recently been expanded to treat diseases such as cancer, rheumatoid arthritis, and Alzheimer's by targeting self-antigens. The effectiveness and safety of the vaccine depends upon the appropriate activation of T and B cells by specific epitopes within the peptide sequences of the target and carrier sequences.

Type 2 Diabetes Mellitus (T2DM) is increasingly recognized as a major health problem worldwide. Long-term (T2DM), however, leads to peripheral arterial disease (PAD), diabetes neuropathy, and cardiovascular disease (CVD). The success of treatment is limited by inconsistent drug intake and the economic burden associated with lifelong treatment.

vWF is a causal factor for insulin resistance (IR), inhibition of nitric oxide (NO) synthesis, and primary hemostasis, as well as macrovascular complications like peripheral arterial disease (PAD), myocardial infarction (MI), and stroke. It is also a prognostic marker for different pathological conditions, i.e., chronic obstructive pulmonary disease (COPD), hypertension, and diabetes mellitus (DM), where endothelial dysfunction (ED) is one of the prominent features.

Thus, a vaccine composition for treating or inhibiting insulin resistance (IR) solving the aforementioned problems is desired.

SUMMARY

In an embodiment, the present subject matter relates to a composition for treating or preventing insulin resistance in a subject, the composition comprising a peptide of SEQ ID NO: 1 and a pharmaceutically acceptable carrier or adjuvant. In an embodiment, the composition can be a vaccine composition or a peptide composition.

According to an embodiment, a method of treating or preventing insulin resistance can include administering a therapeutically effective amount of a composition comprising a peptide of SEQ ID NO: 1 and a pharmaceutically acceptable carrier or adjuvant.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a composition for treating or preventing insulin resistance in a subject, the composition comprising a peptide of SEQ ID NO: 1 and a pharmaceutically acceptable carrier or adjuvant. In an embodiment, the composition can be a vaccine composition or a peptide composition.

Diabetes mellitus (DM) has been associated with increased vWF release and decreased NO production. Nitric oxide (NO) is a second messenger of insulin action that induces glucose uptake in cells. It has now been found, based on SWISS molecular modeling studies, that the C-terminal region of the vWF (loop 2 amino acids 2730-2783) (SEQ ID NO: 1) perfectly fits the insulin receptor, where insulin usually binds, and that vWF and insulin bind at the same site at the insulin receptor. Accordingly, the binding of vWF to the insulin receptor inhibits nitric oxide (NO) production and induces insulin resistance (IR). Thus, restoring nitric oxide (NO) production can increase glucose uptake and, thereby, decrease IR.

According to an embodiment, the present compositions can increase nitric oxide (NO) production by preventing binding of vWF to the insulin receptor. For example, the present vaccine compositions can induce B cells to secrete anti-vWF antibodies capable of neutralizing an insulin receptor biding portion of vWF or the specific region of vWF that binds to the insulin receptor. Neutralization of vWF in this manner can induce or facilitate glucose uptake by promoting nitric oxide (NO) production.

Accordingly, in one embodiment, a method of treating or preventing insulin resistance can include administering a therapeutically effective amount of a composition comprising a peptide of SEQ ID NO: 1 and a pharmaceutically acceptable carrier or adjuvant.

As used herein, the term "pharmaceutically acceptable carrier" refers to any ingredient having no therapeutic activity and being nontoxic and thus suitable as carrier. Nonexclusive suitable carriers will include any of the carriers commonly used in pharmaceutical products, such as, for example, water for injections, microcrystalline cellulose, lactose and starch.

As used herein, the term "pharmaceutically acceptable adjuvant" refers to a substance that enhances, augments or potentiates the host's immune response' to an antigen, in this case the peptide having the amino acid sequence SEQ ID NO: 1. Such adjuvants include, but are not limited to, mineral oil emulsions; aluminum hydroxide; cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); detoxified mutants of a bacterial ADP-ribosylating toxin such as a cholera toxin (CT), a pertussis toxin (PT), or an E. coli heat-labile toxin (LT);

polymers, co-polymers such as polyoxyethylene-polyoxypropylene copolymers, including block co-polymers; polymer PI 005; Freund's complete adjuvant (for animals); Freund's incomplete adjuvant; sorbitan monooleate; squalene; CRL-8300 adjuvant; alum; QS 21, muramyl dipeptide; CpG oligonucleotide motifs and combinations of CpG oligonucleotide motifs; trehalose; bacterial extracts, including mycobacterial extracts; detoxified endotoxins; membrane lipids; or combinations thereof. A suitable adjuvant may be selected by one ordinary skilled in the art with the use of the guideline in the field of adjuvants. Hackett C J, Harn D A. Vaccine adjuvants: immunological and clinical principles. 2006.

In some embodiments, the vaccine compositions include from about 0.001 to 20 wt. % of the peptide of SEQ ID NO: 1.

The vaccine composition can include optional ingredients. Such optional ingredients generally are used individually at levels from about 0.0005% to about 10.0%, preferably from about 0.005% to about 1.0% by weight of the composition.

The vaccine compositions can be prepared by standard techniques well known to those skilled in the art. Such procedures include, but are not limited to, mixing the peptide of SEQ ID NO: 1 with other ingredients of the composition in a conventional manner. Accordingly, the peptide can be formulated as a vaccine composition using adjuvants, pharmaceutically acceptable carriers, excipients, diluents, auxiliary agents, or other ingredients routinely provided in vaccine compositions. Such formulations are readily determined by one of ordinary skill in the art and include formulations for immediate release and for sustained release, e.g., microencapsulation. The present vaccine compositions can be administered by any convenient route including subcutaneous, intramuscular, oral, oromucosal, or other parenteral or internal route. Similarly, the vaccines can be administered as a single dose or divided into multiple doses for administration. Immunization schedules are readily determined by the one ordinary skilled in the art.

In practicing the present methods, an immunizing effective amount of the vaccine compositions may be administered by a variety of routes including, but are not limiting to, injections, e.g. subcutaneous, intramuscular, or intravenous; topical application to the mucosal epithelia; intranasal, and oral administration. Effective amounts of the vaccine composition may vary on animal species and route of administration and is expected to vary from about 0.001 mg/kg body weight per day to about 100 mg/kg per day.

Examples of suitable optional ingredients include, but are not limited to, solvents, buffers, emulsifiers, and preservatives.

In one experiment, polyclonal anti-vWF antibodies were administered to an animal for specifically neutralizing the vWF. Then, nitric oxide (NO) was measured (by the oxyhemoglobin method) and glucose uptake was measured (by the C14 glucose uptake method). It was found that anti-vWF antibody treatment restored insulin-induced NO production and, consequently, C14 glucose uptake, as well as improve IR (measured by HOMA-IR,GTT,ITT).

In another experiment, a recombinant vWF protein with a specific vWF sequence (SEQ ID NO: 1) was found to significantly inhibit NO production as well as glucose uptake. This suggests that anti-vWF antibodies neutralize the specific vWF sequence and restore NO production and glucose uptake.

It is to be understood that the present methods and compositions are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A composition for treating or preventing insulin resistance, comprising a peptide consisting of SEQ ID NO: 1 and an adjuvant.

2. A method for inhibiting or preventing insulin resistance, comprising administering a therapeutically effective amount of the composition of claim 1 to a subject in need thereof.

3. The method of claim 2, wherein the composition induces B cell secretion of polyclonal antibodies for neutralizing an insulin receptor binding portion of Von Willebrand Factor (vWF).

4. A method for increasing nitric oxide production in a subject, comprising administering a therapeutically effective amount of the composition of claim 1 to a subject in need thereof.

5. A method for treating or preventing insulin resistance, comprising administering a therapeutically effective amount of a composition comprising a peptide consisting of SEQ ID NO: 1 and a pharmaceutically acceptable carrier or adjuvant to a subject in need thereof.

6. A method for increasing nitric oxide production in a subject, comprising administering a therapeutically effective amount of a composition comprising a peptide consisting of SEQ ID NO: 1 to a subject in need thereof.

* * * * *

```
                            SEQUENCE LISTING

Sequence total quantity: 1
SEQ ID NO: 1            moltype = AA  length = 53
FEATURE                 Location/Qualifiers
source                  1..53
                        mol_type = protein
                        organism = Homo sp.
SEQUENCE: 1
EPECNDITAR LQYVKVGSCK SEVEVDIHYC QGKCASKAMY SIDINDVQDQ CSC          53
```